(12) United States Patent
Ogawa (10) Patent No.: US 7,336,768 B2
(45) Date of Patent: Feb. 26, 2008

(54) X-RAY DIAGNOSIS APPARATUS

(75) Inventor: Kenichi Ogawa, Tochigi-ken (JP)

(73) Assignee: Kabushiki Kaishi Toshiba, Tokyo (JP)

( * ) Notice: Subject to any disclaimer, the term of this patent is extended or adjusted under 35 U.S.C. 154(b) by 0 days.

(21) Appl. No.: 11/539,544

(22) Filed: Oct. 6, 2006

(65) Prior Publication Data

US 2007/0211851 A1   Sep. 13, 2007

Related U.S. Application Data

(63) Continuation of application No. 10/609,646, filed on Jul. 1, 2003, now abandoned.

(30) Foreign Application Priority Data

Jul. 8, 2002   (JP)   ............................ 2002-198148

(51) Int. Cl.
  *G21K 3/00*   (2006.01)
  *H05G 1/06*   (2006.01)
(52) U.S. Cl. ...................... 378/156; 378/196
(58) Field of Classification Search ........ 378/145–153, 378/156–160, 193, 196, 197
  See application file for complete search history.

(56) References Cited

U.S. PATENT DOCUMENTS

| 4,766,603 | A | * | 8/1988 | Okabe et al. ............... 378/152 |
|---|---|---|---|---|
| 4,776,603 | A | | 10/1988 | Watts |
| 5,369,678 | A | * | 11/1994 | Chiu et al. ..................... 378/62 |
| 5,377,252 | A | | 12/1994 | Liebetruth |
| 5,630,414 | A | | 5/1997 | Horbascheck |
| 6,148,062 | A | * | 11/2000 | Romeas ..................... 378/156 |
| 6,173,033 | B1 | | 1/2001 | Klingenbeck-Regan et al. |
| 6,445,761 | B1 | | 9/2002 | Miyazaki et al. |
| 6,480,570 | B1 | | 11/2002 | Ikeda |
| 6,618,466 | B1 | | 9/2003 | Ning |

FOREIGN PATENT DOCUMENTS

JP   2000-354593   12/2000

* cited by examiner

*Primary Examiner*—Edward J. Glick
*Assistant Examiner*—Irakli Kiknadze
(74) *Attorney, Agent, or Firm*—Oblon, Spivak, McClelland, Maier & Neustadt, P.C.

(57) ABSTRACT

An X-ray diagnosis apparatus is configured to control at least one of the X-ray diaphragm which restricts the irradiation range of the X-ray and the compensation filter which attenuates the amount of the X-ray based on at least one of the rotation position or the position parallel to the body axis of the X-ray source.

33 Claims, 11 Drawing Sheets

| Y POSITION SUPPROT -ING UNIT | X POSITION X-RAY DIAPHR- AGM | Y POSITION X-RAY DIAPHR- AGM | X POSITION COMPEN- SATION FILTER | φ ANGLE COMPEN- SATION FILTER | α SORT COMPEN- SATION FILTER |
|---|---|---|---|---|---|
| K1 | C1 | L1 | X1 | φ1 | RECTANGLE |
| K2 | C2 | L2 | X2 | φ2 | TRAPEZIUM |
| | | | | | |
| | | | | | |
| Kn | Cn | Ln | Xn | φn | ELLIPTICAL |

X-RAY DIAGNOSIS APPARATUS

CROSS-REFERENCE TO RELATED APPLICATIONS

This application is a continuation of, based upon and claims the benefit of priority under 35 U.S.C. § 120 from U.S. Ser. No. 10/609,646, filed Jul. 1, 2003, which claims the benefit of priority under 35 U.S.C. § 119 from Japanese Patent Application No. 2002-198148, filed Jul. 8, 2002, the entire contents of each which are incorporated herein by reference.

FIELD OF THE INVENTION

The present invention relates to an X-ray diagnosis apparatus and a method for creating an X-ray image.

BACKGROUND OF THE INVENTION

A conventional X-ray diagnosis apparatus irradiates an X-ray from an X-ray tube to a patient, and detects the X-ray penetrated through the patient with an image intensifier (hereinafter referred to as I.I.), which changes the X-ray into a light and an imaging tube or a charge coupled device changes the light into an electronic signal or a flat panel detector (hereinafter called as a FPD) directly changes the X-ray into the electronic signal. Thus, an X-ray fluoroscopic image is obtained. The X-ray apparatus enables an operator to observe flow and movement of a contrast agent inside the patient on a display. Moreover, the fluoroscopic image is stored in a memory and used for various image processes, such as enlargement/contrast adjustment/space filter processes or minimum/maximum trace processes or subtraction process or adding process for removing a noise, and the like.

The subtraction process for obtaining a subtraction image of a part of the patient using the X-ray diagnosis apparatus is explained below. In order to perform the subtraction process, the fluoroscopic image, a mask image, and a contrast image are obtained. The fluoroscopic image is used for setting a position of an X-ray diaphragm and a compensation filter. The mask image and the contrast image are basic images to create the subtraction image. Hereinafter, an imaging for obtaining the fluoroscopic image is called a fluoroscopic imaging, and an imaging for obtaining a mask image and a contrast image is called a main imaging. In the fluoroscopic imaging, the operator sets X-ray fluoroscopic terms (X-ray tube voltage, X-ray tube current, fluoroscopic time, etc.), considering patient information, such as a patient age, sex, the portion of the body being imaged and other factors (such as, but not limited to, patient condition, pregnancy status, medical conditions, allergy to the contrast agent, specific needed nursing care). The X-ray is irradiated to the patient based on the fluoroscopic factors, and the fluoroscopic image is displayed on the display. The operator adjusts a position of a supporting unit for supporting the X-ray tube and the I.I., in order to position an imaging area at an appropriate part of the patient. The operator sets positions of the X-ray diaphragm and the compensation filter, observing the fluoroscopic image.

The main imaging starts after the X-ray diaphragm and the compensation filter are set. In the main imaging, the mask image and the contrast image are obtained in order. The mask image is aligned to the contrast image, and the subtraction process between these images is performed. The subtraction image is displayed on the display in a real time.

In the conventional X-ray diagnosis apparatus, the X-ray diaphragm and the compensation filter are fixed at such a position that the imaging area is adequate during the main imaging, such as during a bolus chase imaging where the X-ray and the I.I. automatically move. That is, wherever the X-ray tube and the I.I. move within the imaging area, the X-ray irradiated to the patient is not blocked or attenuated. However, since the X-ray diaphragm is fixed during the main imaging, the irradiation range of the X-ray is wide, the amount of the X-ray irradiated to the patient increases, and the influence of scattered X-ray appears. Moreover, since the compensation filter is fixed during the main imaging, X-ray halation partially remains. However, it is difficult to manually adjust the position of the X-ray diaphragm or the compensation filter according to a contour of the patient during the main imaging where the X-ray tube and the I.I. automatically move.

SUMMARY OF THE INVENTION

The present invention intends to solve the above-mentioned problems. One aspect of the present invention is an X-ray diagnosis apparatus including an X-ray source configured to irradiate an X-ray to an object, a diaphragm configured to restrict an irradiation range of the X-ray, a detector configured to detect the X-ray penetrated through the object, a bed configured to support the object, a mechanism configured to move a position of the X-ray source in a direction taken along the bed, and a controller configured to control the diaphragm based on the position of the X-ray source in the direction.

Another aspect of the present invention is an X-ray diagnosis apparatus including an X-ray source configured to irradiate an X-ray to an object, a diaphragm configured to restrict irradiation range of the X-ray, a detector configured to detect the X-ray penetrated through the object, a bed configured to support the object, a mechanism configured to rotate a position of the X-ray source around the bed, and a controller configured to control the diaphragm based on the position of the X-ray source.

Another aspect of the present invention is an X-ray diagnosis apparatus including an X-ray source configured to irradiate an X-ray to an object, a compensation filter configured to attenuate an amount of the X-ray, a detector configured to detect the X-ray penetrated through the object, a bed configured to support the object, a mechanism configured to move a position of the X-ray source in a direction taken along the bed, and a controller configured to control the compensation filter based on the position of the X-ray source in the direction.

Another aspect of the present invention is an X-ray diagnosis apparatus including an X-ray source configured to irradiate an X-ray to an object, a compensation filter configured to attenuate an amount of the X-ray, a detector configured to detect the X-ray penetrated through the object, a bed configured to support the object, a mechanism configured to rotate a position of the X-ray source around the bed, and a controller configured to control the compensation filter based on the position of the X-ray.

Another aspect of the present invention is an X-ray diagnosis apparatus including an X-ray source configured to irradiate an X-ray to an object, a compensation filter configured to attenuate an amount of the X-ray, a detector configured to detect the X-ray penetrated through the object, a bed configured to support the object, a mechanism configured to move a position of the X-ray source to parallel to the bed, and a controller configured to control the compensation filter to move in an opposite direction to a direction of movement of the X-ray source at the same speed as the movement of the X-ray source such that the compensation filter relatively stops to the bed.

Another aspect of the present invention is a method for obtaining an X-ray image including irradiating an X-ray to an object, restricting an irradiation range of the X-ray, detecting the X-ray penetrated through the object, moving a position of the X-ray source in a direction taken along the bed, and controlling the diaphragm based on the position of the X-ray source in the direction.

BRIEF DESCRIPTION OF THE DRAWINGS

A more complete appreciation of the invention and many of the attendant advantages thereof will be readily obtained as the same becomes better understood by reference to the detailed description when considered in connection with the accompanying drawings. Wherever possible, the same reference numbers will be used throughout the drawings to refer to like parts. In the drawings.

DETAILED DESCRIPTION OF THE INVENTION

Figure 1:
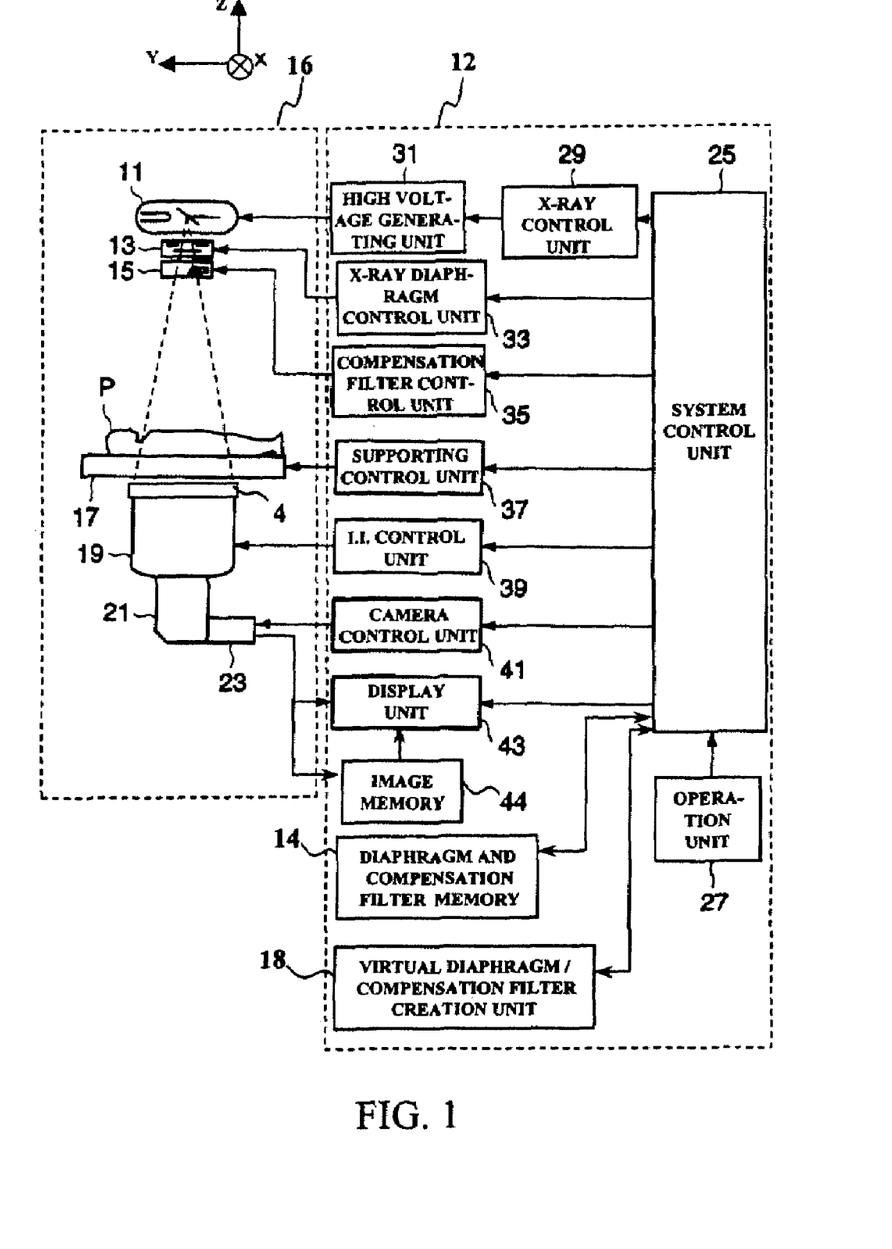
FIG. 1 is a block diagram of an X-ray diagnosis apparatus in a first embodiment.

A first embodiment of the present invention is explained referring to the figures. FIG. 1 is a block diagram of an X-ray diagnosis apparatus. The X direction is approximately parallel to a width direction of a patient, the Y direction is approximately parallel to a body axis of the patient, and the Z direction is approximately parallel to a thickness direction of the patient. As shown in FIG. 1, an X-ray diagnosis apparatus includes a supporting unit 16 and a main control unit 12. The supporting unit 16 includes a C-arm and a bed 17. An X-ray tube 11 that irradiates an X-ray is mounted on one side of the C arm, and an X-ray diaphragm unit 13 that blocks the X-ray irradiated to an unnecessary area is provided on a patient P side of the X-ray tube 11. A compensation filter unit 15 that attenuates the X-ray to restrain halation is also provided on the patient P side of the X-ray tube 11. On the opposite side of the C-arm to the bed 17, an X-ray grid 4, which cuts a scattering X-ray penetrated through the patient P; an I.I. 19, which changes the remaining X-ray to an optical image; an optical unit 21, which corrects a size of the optical image; and a TV camera (or CCD, for example) 23, which changes the optical image to a TV image signal, are mounted.

The main control unit 12 includes a system control unit 25; an X-ray control unit 29, which controls a high voltage generating unit 31 to generate high voltage impressed to the X-ray tube 11; an X-ray diaphragm control unit 33, which controls the degree (X, Y direction) of opening between X-ray diaphragms; and a compensation filter control unit 35, which controls a position (X direction); a rotation angle φ, and a type of a compensation filter in the compensation filter unit 15. Moreover, the main control unit 12 includes a supporting control unit 37 that controls a position (Y direction) of the C-arm to the bed 17, an I.I. control unit 39 that controls the I.I. 19, a camera control unit 41 that controls the TV camera 23, an image memory 44 that stores an X-ray image obtained by the TV camera 23. Furthermore, the main control unit 12 includes a display unit 43 that displays the X-ray image obtained by the TV camera 23, a diaphragm, and compensation filter memory 14 that stores a position, etc. of the X-ray diaphragm and the compensation filter, a virtual diaphragm/compensation filter creation unit 18, which creates a graphic image of the X-ray diaphragm and the compensation filter on the display unit 43, and an operation unit 27 (for example, a keyboard and a mouse, or the like), which allows an operator to input instructions.

Figure 2:
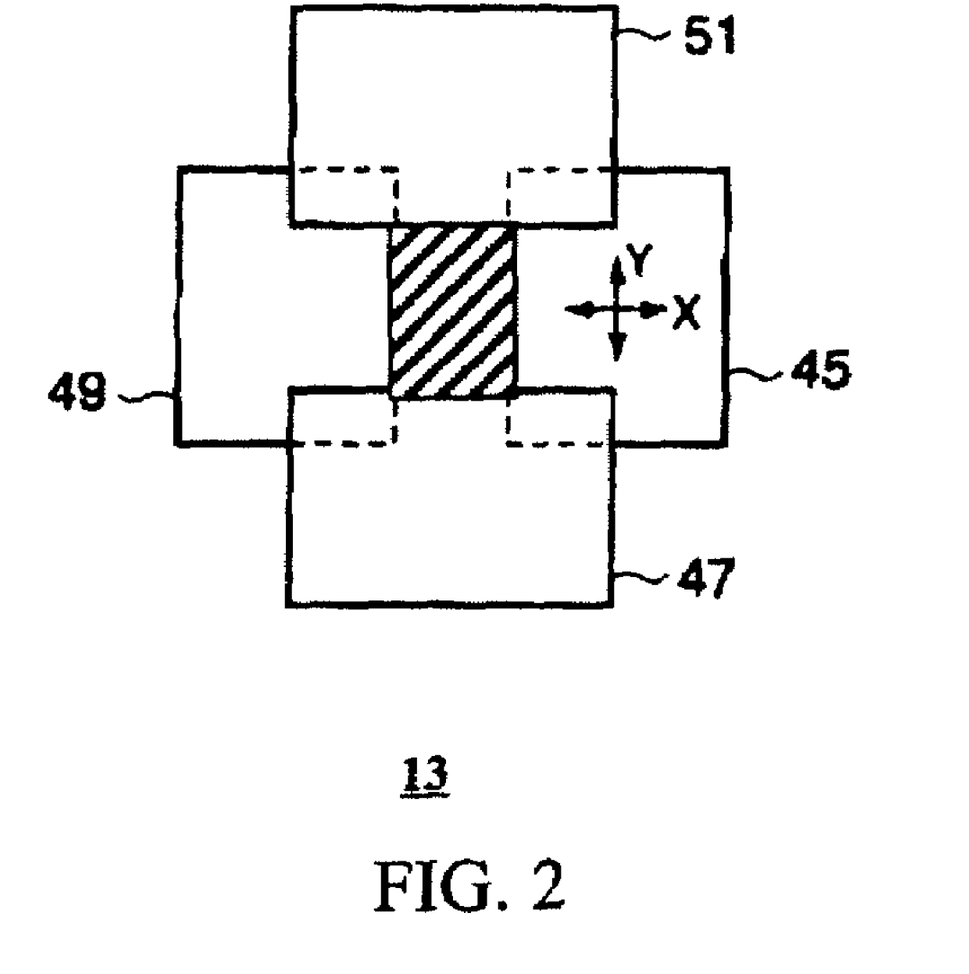
FIG. 2 is a top view of an X-ray diaphragm unit of the X-ray diagnosis apparatus in the first embodiment.

The X-ray diaphragm unit 13 is explained in detail, referring to FIG. 2, which is a top view of the X-ray diaphragm unit 13 from the X-ray tube 11. The X-ray diaphragm unit 13 has a plurality of X-ray diaphragms 45, 47, 49, and 51. These diaphragms may be made of lead, for example, which limits the X-ray. The X-ray diaphragm 45 and 49 symmetrically move, and the X-ray diaphragms 47 and 51 symmetrically move. In FIG. 2, the X-ray diaphragms 47 and 51 are arranged at a back side and the X-ray diaphragms 45 and 49 are arranged at a near side. An area (indicated as dotted lines) surrounded by the X-ray diaphragms shows an area where the X-ray irradiated from the X-ray tube 11 passes, and the X-ray diaphragms 45, 47, 49, and 51 symmetrically and asymmetrically move to extend or narrow the pass area. Thus, the irradiation area of the X-ray to the patient P may be controlled.

Figure 3A:
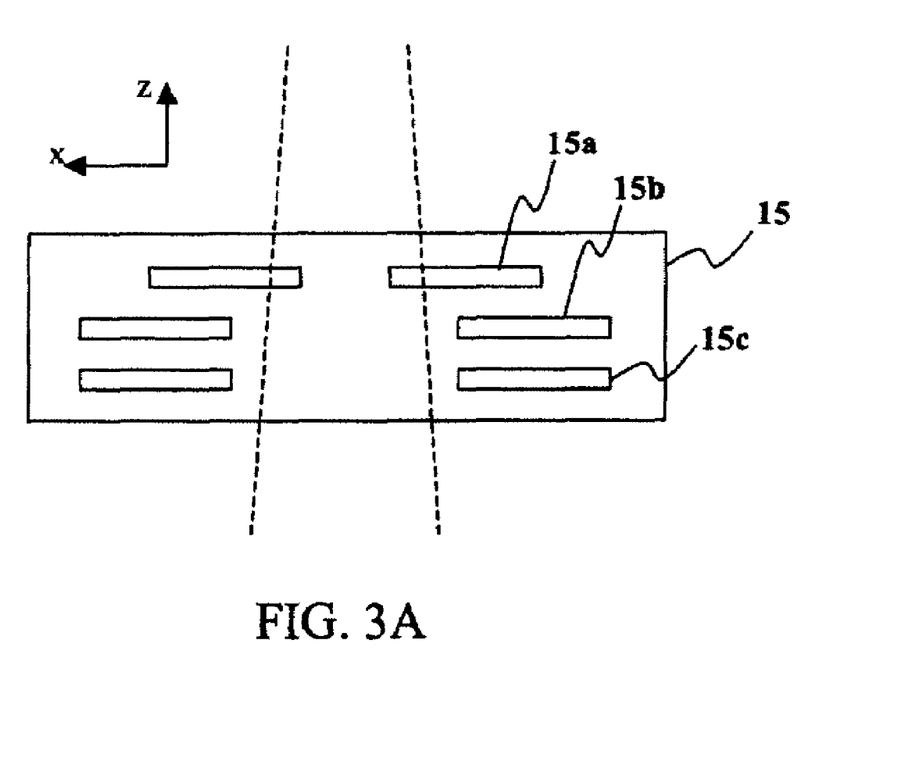
FIG. 3A is a sectional view of a compensation filter unit.
Figure 3B:
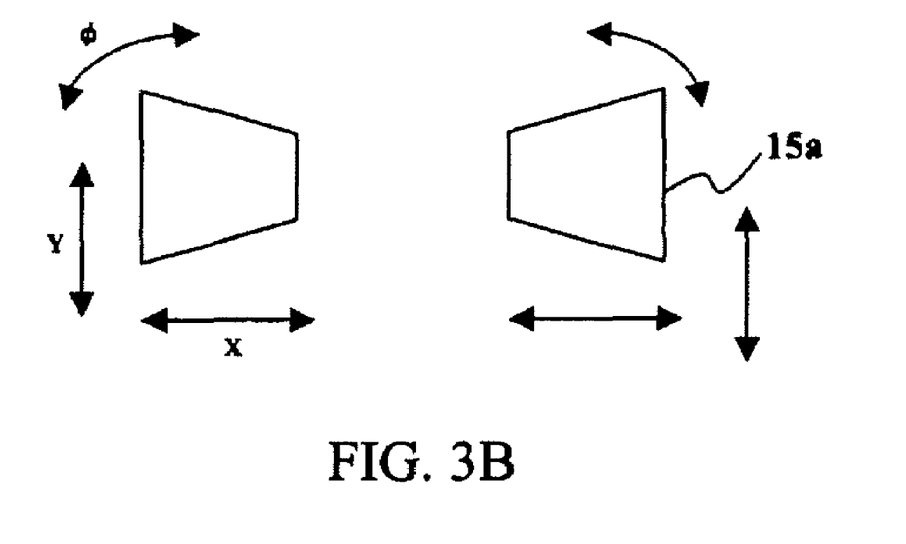
FIG. 3B is a top view of the compensation filter.

With reference to FIGS. 3A and 3B, the compensation filter unit 15 is explained in detail. The non-limiting illustration of FIG. 3A shows a sectional view of the compensation filter unit 15 from the body axis of the patient P, and FIG. 3B shows a top view from the X-ray tube 11. The compensation filter unit 15 includes a plurality of types of the compensation filters 15a, 15b, and 15c, which are arranged along the direction of the X-ray irradiation (indicated as dotted lines). The compensation filter 15c is far from the X-ray tube 11, and the compensation filter 15a is near the X-ray tube 11. Generally, each compensation filter is made of, for example, acrylic or the like. Forms of the compensation filters 15a through 15c may be different from each other.

For example, the compensation filter 15b may have an elliptical form and the compensation filter 15c may have a rectangular form. In the non-limiting illustration of FIG. 3B, the compensation filter 15a is illustrated in the shape of a trapezium. These compensation filters 15a, 15b, and 15c move in the X and Y directions and rotates on a X-Y plate (the rotation angle is shown as φ). One or more of the compensation filters move to interrupt and attenuate the X-ray. In FIG. 3A, the case where the compensation filter 15a interrupts the X-ray is shown.

Next, an operation of the X-ray diagnosis apparatus is explained in the order of the fluoroscopic imaging, a setup of the X-ray diaphragm/compensation filter, and the main imaging.

Figure 4:
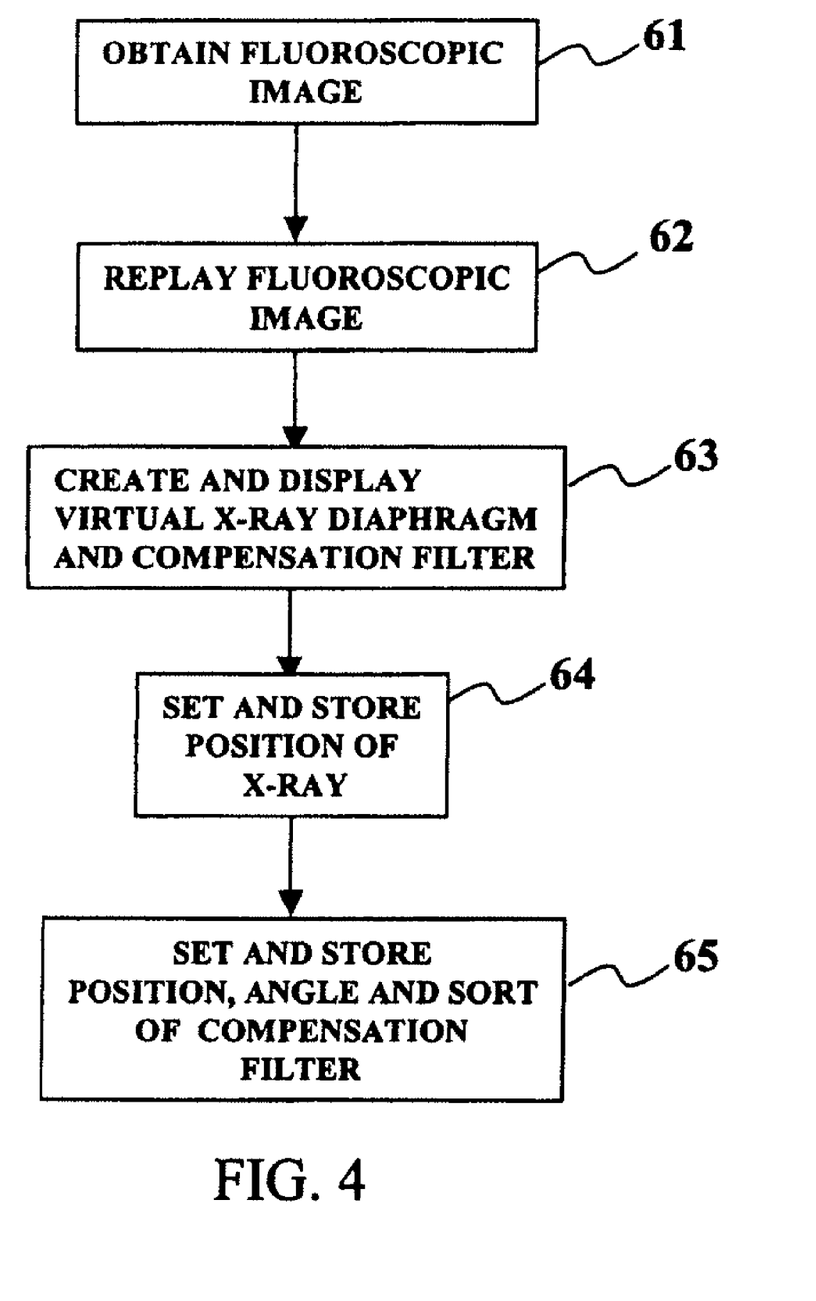
FIG. 4 is a flow chart for setting an X-ray diaphragm and a compensation filter in the first embodiment.

The fluoroscopic imaging and the setup of the X-ray diaphragm/compensation filter is explained with reference to the non-limiting illustration of FIG. 4, which is a flow chart. In the first embodiment, so-called bolus chase imaging is explained as one example. The bolus chase imaging is that the C-arm slides along a longitudinal direction of the bed 17 without rotation, and a contrast agent injected into the patient P is imaged. In Step 61 of FIG. 4 showing the fluoroscopic imaging, the operator (generally a doctor or a radiological technician) checks information (such as a patient name or other relevant information) about the patient P, the operator inputs suitable X-ray fluoroscopic terms (such as X-ray tube voltage, X-ray tube current, fluoroscopic time, or other appropriate parameters) for the patient P via the operation unit 27, and the operator puts the patient P on the bed 17.

In general, the X-ray tube current in the fluoroscopic imaging is lower than that of the main imaging, and is set up to an appropriate value by auto brightness control (ABC). The system control unit 25 controls the X-ray tube 11 to irradiate the X-ray to the patient P on the bed 17 via the X-ray control unit 29 and the high voltage generating unit 31. At that time, the X-ray diaphragm control unit 33 controls the X-ray diaphragms 45, 47, 49, and 51 of the X-ray diaphragm unit 13 so that the pass area of the X-ray is the maximum. Similarly, the compensation filters 15a through 15c of the compensation filter unit 15 are held at positions such that the X-ray is not attenuated.

The X-ray penetrates through the patient P, and the scattered X-ray is cut by the X-ray grid 4. The remaining X-ray is irradiated to the I.I. 19. In the I.I. 19, the optical signal corresponding to the amount of the incident X-ray is generated, and after the optical signal is corrected by the optical unit 21, the corrected optical signal is changed to the electric signal as the TV image signal by the TV camera 23. The TV image signal is changed to a digital signal by an A/D converter and the image processing performs on the digital signal. The processed digital signal is converted to a TV image signal to be displayed on the display unit 43 as the X-ray fluoroscopic image. Observing the X-ray fluoroscopic image on the display unit 43, the operator may move the C-arm from (for example) an abdomen to a lower leg of the patient P by the operation unit 27 and the supporting control unit 37. At that time, the X-ray continues to irradiate the X-ray to the patient P, and the fluoroscopic image from the abdomen to the lower leg of the patient P is displayed on the display unit 43 in a real time. The X-ray fluoroscopic image is stored in the image memory 44. A similar operation is performed in the main imaging.

Setup (Step 62 through Step 65 in FIG. 4) of the X-ray diaphragm unit/compensation filter are explained. When the setup is performed, the X-ray is not irradiated from the X-ray tube 11. In Step 62 for replaying the fluoroscopic image, the fluoroscopic image data is read out from the image memory unit 44 to be displayed on the display unit 43.

Figure 5:
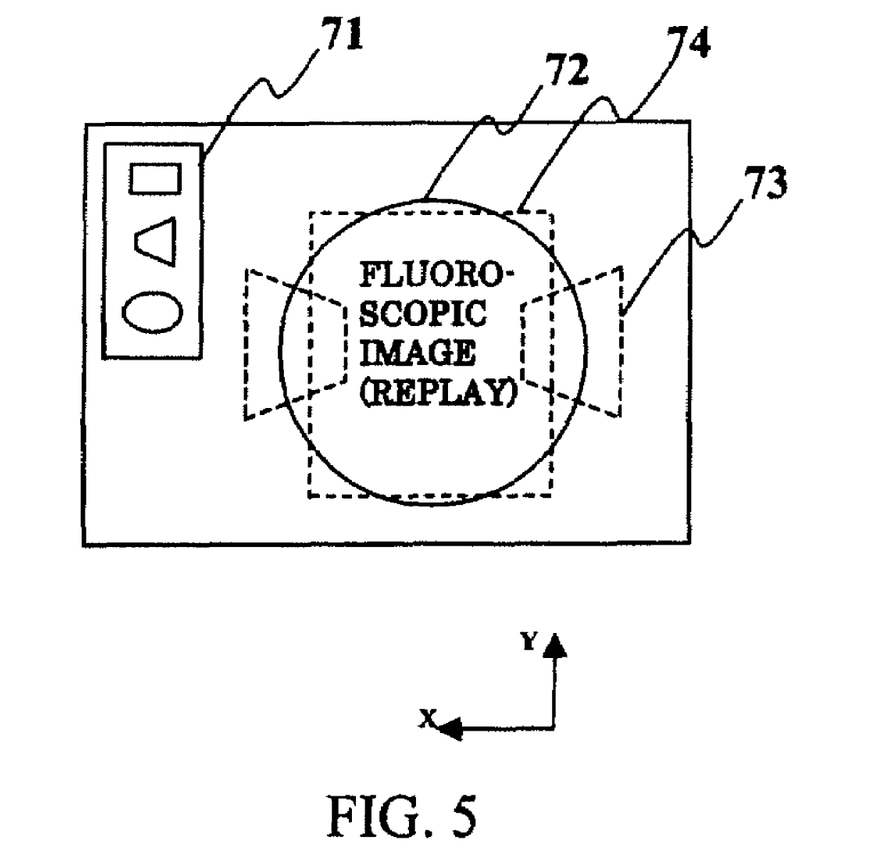
FIG. 5 is an illustration of an example displayed on a display unit in the first embodiment.

FIG. 5 shows an example displayed on the display unit 43. The fluoroscopic image replays in a center of a monitor as a circular image. In Step 63, the virtual X-ray diaphragm and virtual compensation filter are created on the fluoroscopic image 72 by the virtual diaphragm/compensation filter creation unit 18. The virtual X-ray diaphragm is a graphic displayed on the display unit 43, and one example is indicated by dotted lines 74 in FIG. 5. The virtual compensation filter is a graphic displayed on the display unit 43 similarly, and one example is indicated by dotted lines 73 in FIG. 5. A scale of the virtual X-ray diaphragm and virtual compensation filter correspond to a scale of the X-ray fluoroscopic image. When the X-ray fluoroscopic image is enlarged, the virtual X-ray diaphragm and virtual compensation filter are similarly enlarged. In Step 64, the operator sets X and Y positions of the X-ray diaphragms.

In detail, the operator adjusts a size of the virtual X-ray diaphragm 74 on the monitor, by the operation unit 27. According to the size of the adjusted virtual X-ray diaphragm 74, X and Y position data of the X-ray diaphragms is calculated, and the position data is stored in the diaphragm and compensation filter memory 14 with the position data of the supporting unit 16. In Step 65, a position, an angle, and a sort of the compensation filter is set up. In detail, the operator selects one virtual compensation filter among candidates shown as icons 71 on the monitor.

The case where a virtual compensation filter in the center of the candidates is selected is explained below. The selected virtual compensation filter is displayed near the fluoroscopic image 72 on the monitor. The operator adjusts the X position of the virtual compensation filter 73 and also adjusts the angle of the virtual compensation filter 73. The type, position, and angle of the virtual compensation filter is stored in the diaphragm and compensation filter memory 14 with the position data of the supporting unit 16. Similarly, the operation unit 27 is used for selecting or adjusting the type, position, and angle of the virtual compensation filter.

Figure 6:
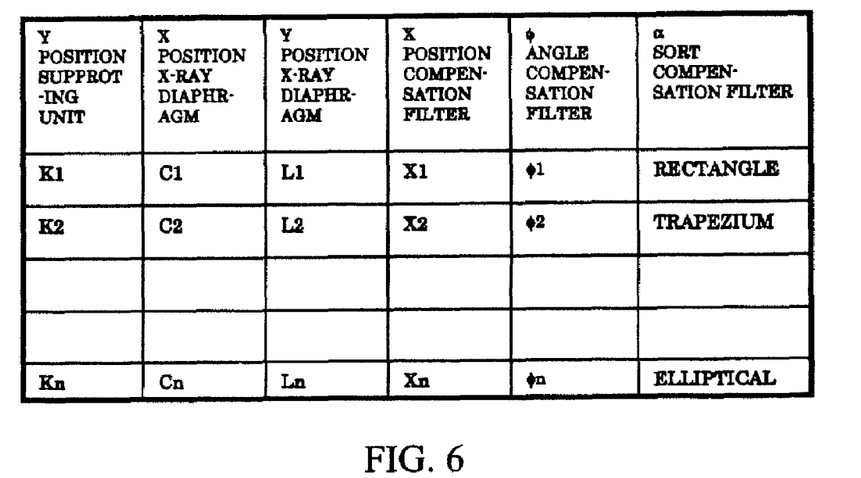
FIG. 6 is a table stored in a diaphragm and compensation filter memory in the first embodiment.

After the setup is completed, the operator sets the X-ray diaphragm and compensation filter on another replayed fluoroscopic image of a different position. The operator sets the X-ray diaphragm and compensation filter on a whole imaging area (or only on a desired area). Thus, the X-ray diaphragm and compensation filter may be set, and a table of data (as shown, for example, in FIG. 6) is stored in the diaphragm and compensation filter memory 14. The Y position of the supporting unit may be a position of the X-ray tube 11 which may be an absolute position which is not related to the bed 17 or a relative position to the bed 17. The Y position of the X-ray tube may be a position of the I.I. or the C-arm, etc.

An operation of the main imaging is explained below. As described above, the main imaging is performed to obtain the mask image and the contrast image used for the subtraction process. The imaging for obtaining the mask image starts based on the instruction of the operator and is performed before the contrast agent is injected into the patient P. The X-ray tube 11 and the I.I. 19 automatically move from the abdomen to the lower leg or from the lower leg to the abdomen. After the mask image is obtained, the imaging for obtaining the contrast image starts. The imaging starts immediately after the contrast agent is injected into the patient P, based on the instruction of the operator. In the imaging for obtaining the contrast image, the X-ray tube 11 and the I.I. 19 move along the flow of the contrast agent at an arbitrary speed based on the instruction of the operator. The mask image is aligned to the contrast image and the subtraction process is performed. A trace of the contrast agent, namely a blood vessel, may be emphasized.

Differences between the mask image and the contrast image include the following points, for example. The mask image is obtained before the contrast agent is injected to the patient P, while the contrast image is obtained after the contrast agent is injected to the patient P. The imaging for obtaining the mask image is automatically performed, while the imaging for obtaining the contrast image is performed at arbitrary speed to chase the flow of the contrast agent, and other operations are similar to each other. Additionally, the direction of the imaging for obtaining the mask image may be opposite to or the same as the direction of the imaging for obtaining the contrast image. The imaging for obtaining the contrast image is explained below. An explanation of a similar operation for fluoroscopic imaging is omitted.

Figure 7:
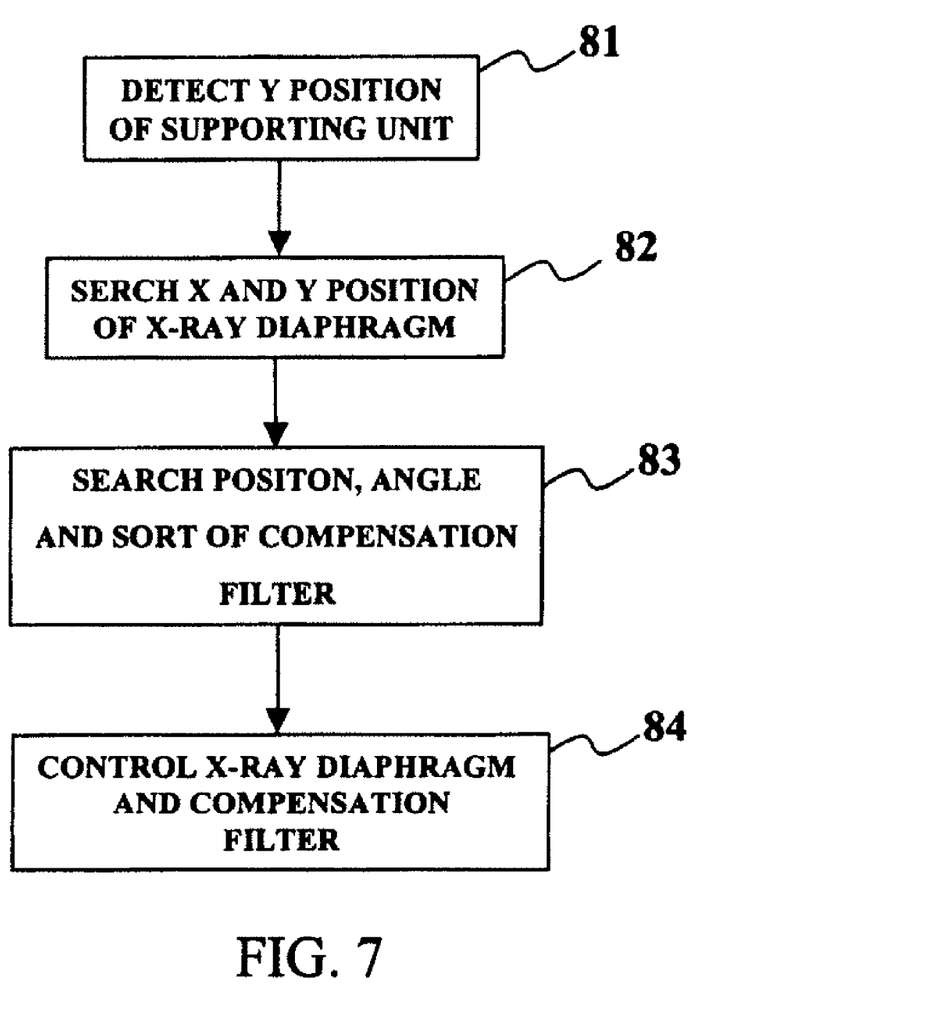
FIG. 7 is a flow chart for obtaining a contrast image in the first embodiment.

FIG. 7 shows a flowchart of operation for obtaining the contrast image. In Step 81, the Y position of the supporting unit 16 is detected by the system control unit 25. In Step 82, the X and Y position of the X-ray diaphragm is searched in the system control unit 25. In detail, the first and second nearest data to the detected Y position is searched from the table shown in FIG. 6, and the X-ray diaphragm data corresponding to the first and second nearest data is specified.

In Step 83, the position, angle and sort of the compensation filter are searched in the system control unit 25. In detail, the data of the compensation filter within a field of view of the I.I. 19 is specified based the detected Y position of the supporting unit 16 and a field of view data of the I.I. 19, which is pre-stored. In Step 84, the X-ray diaphragm and the compensation filter are controlled based on the specified data.

Figure 8A:
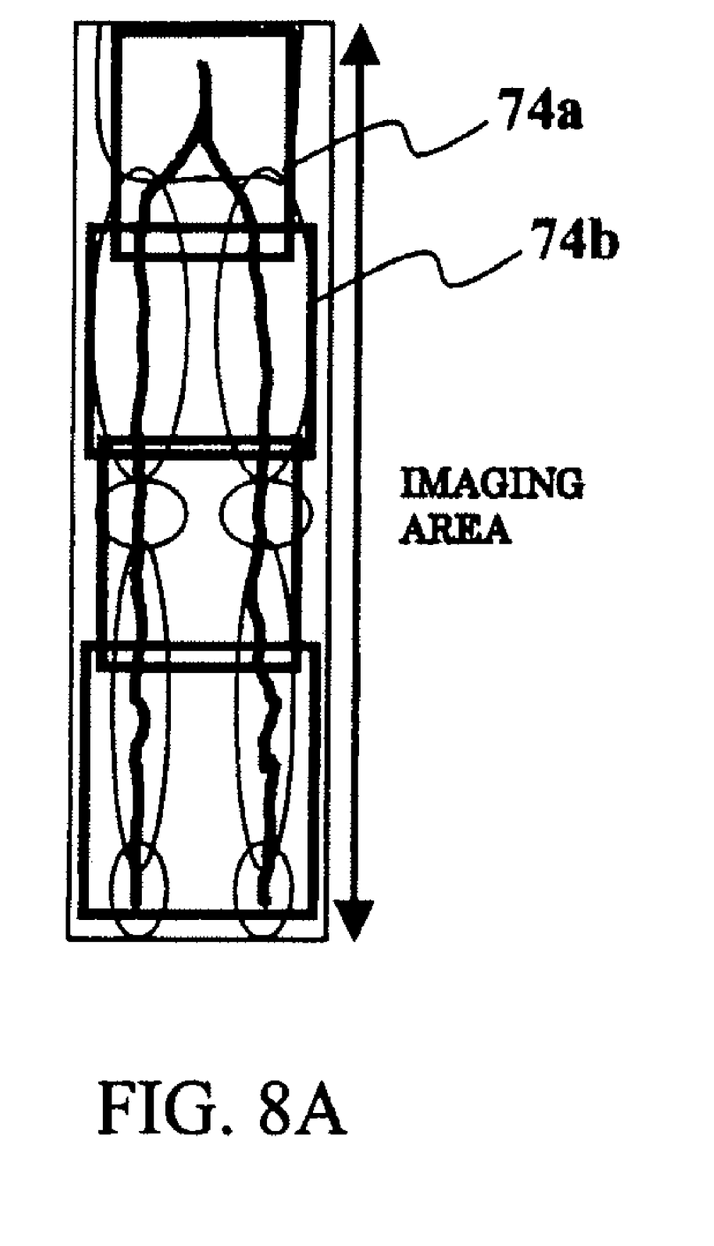
FIG. 8A is an illustration for explaining an operation of the X-ray diaphragm in the first embodiment.
Figure 8B:
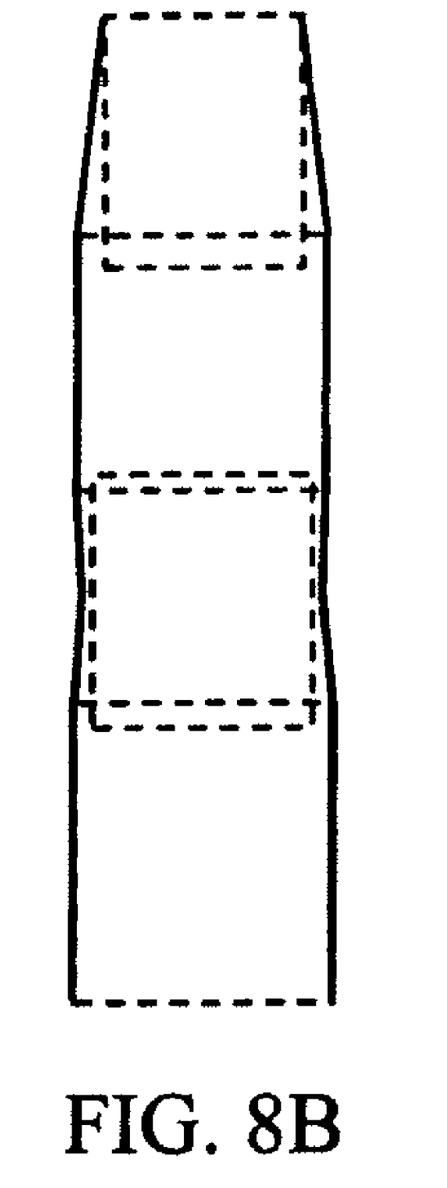
FIG. 8B is an illustration for explaining an X-ray image in the first embodiment.

The control of the X-ray diaphragm is explained with reference to FIGS. 8A and 8B. The controls of the X-ray diaphragm and the compensation filter may be independently performed simultaneously. FIG. 8A shows the fluoroscopic image from the abdomen to the lower leg. In this case, four virtual X-ray diaphragms are set on the fluoroscopic image by the operator. If the detected position of the supporting unit 16 is the position near the abdomen in FIG. 8A, the data 74a and 74b are searched as the X-ray diaphragm data in Step 82. In detail, as shown by solid lines of FIG. 8B, the actual X-ray diaphragms 45, 47, 49, and 51 are controlled as the virtual X-ray diaphragms 74a and 74b, and are connected smoothly. The portions shown as the dotted lines of FIG. 8B indicate the virtual X-ray diaphragms 74 shown as the solid lines of FIG. 8A.

Since the X-ray diaphragm may be controlled as described above, the desired imaging area set by the operator receives adequate X-rays, while the X-ray is appropriately blocked from extraneous areas. In the above explanation, the four virtual X-ray diaphragms are overlapped from the abdomen to the lower leg as shown in FIG. 8A; however, the virtual X-ray diaphragm may be partially set. Where the virtual X-ray diaphragm is not set, the pass area of the X-ray between the X-ray diaphragms may be set as the maximum. That is, the X-ray diaphragm may not block the X-ray, if the virtual X-ray diaphragm is not set as well as the fluoroscopic imaging.

Figure 9:
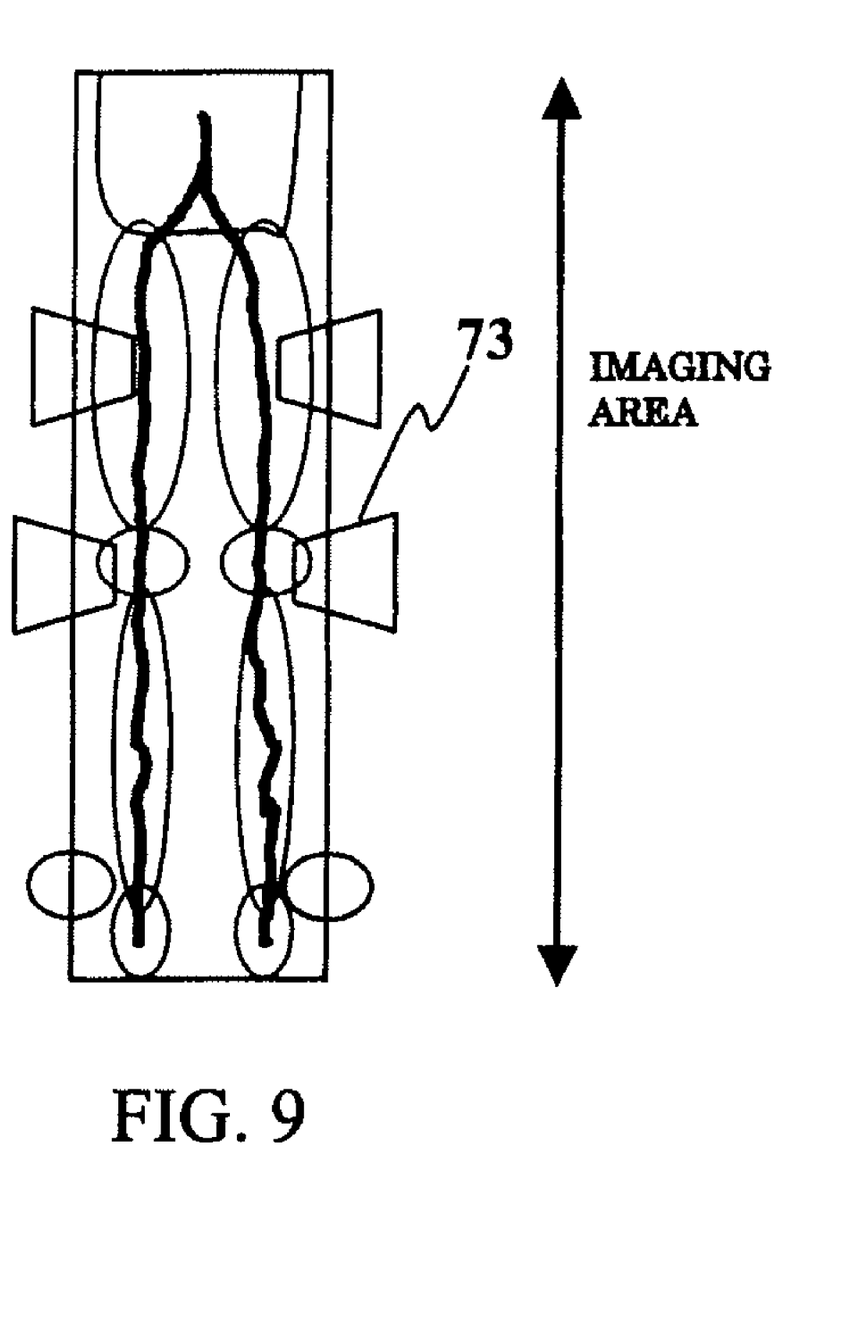
FIG. 9 is an illustration for explaining an operation of the compensation filter.

The control of the compensation filter is explained with reference to FIG. 9, which shows the fluoroscopic image from the abdomen to the lower leg. The non-limiting example where three virtual compensation filters 73 are set on the fluoroscopic image by the operator is shown in FIG. 9. The specified data of the compensation filter in Step 83 is used for controlling the compensation filter as the virtual compensation filter 73 is set. When the X-ray tube 11 moves to the lower leg from the abdomen, the compensation filter moves from the lower leg to the abdomen at the approximately same speed as the X-ray tube 11. The movement of the compensation filter may continue until the compensation filter is beyond the field of view of the I.I 19. Thus, since the compensation filter is controlled to move in an opposite direction to movement direction of the X-ray tube 11 at the approximately same speed, the attenuation of the X-ray is minimized.

After the main imaging, the operator performs an operative treatment on an affected area of the patient P, such as a closed blood vessel, after the operator confirms the affected area on the subtraction image obtained by the main imaging. In detail, while the X-ray is irradiated to the patient and the I.I. detects the X-ray to create the fluoroscopic image again, the operator inserts a catheter into the patient P. During the insertion of the catheter, the operator confirms a position of the catheter on the X-ray fluoroscopic image.

After the operative treatment is completed, the main imaging is preformed on the affected area again. In the main imaging after the operative treatment, the X-ray diaphragm and the compensation filter data used in the main imaging before the operative treatment may be used again. Thus, the operator performs the main imaging after the operative treatment to confirm a result of the operative treatment. The operative treatment may be performed immediately after the operative treatment or may be performed a few days after the operative treatment, for example.

In the first embodiment, since at least one of the X-ray diaphragm and the compensation filter is controlled on the fluoroscopic image according to the position of the X-ray tube, the X-ray diagram or the compensation filter can be set at an appropriate position. In addition, since the virtual X-ray diagram or the virtual compensation filter is used, the X-ray irradiation to the patient may be stopped during setting the X-ray diagram or the compensation, and the amount of the X-ray irradiated to the patient can be reduced.

The present invention is not limited to the above embodiments, and various modifications may be made without departing from the spirit or scope of the general inventive concept. For example, although the X-ray tube and the I.I. move to the bed which is fixed in the first embodiment, the bed may move during the fluoroscopic or main imaging. However, it is more desirable to move the X-ray tube and the I.I. than to move the bed, since the contrast agent may move unusually as a result of the movement of the bed. Moreover, although the X-ray diaphragm can be set in both of the X direction which is perpendicular to the body axis of the patient and the Y direction which is parallel to the body axis of the patient in the first embodiment, the X-ray diaphragm may be set in at least one direction. For example, the X-ray diaphragm data may be stored in only the Y direction of the X-ray diaphragm. Furthermore, although the X-ray diaphragm and the compensation filter are controlled according to the position in the body axis direction (Y direction) of the C-arm in the first embodiment, the C-arm may be fixed in the Y direction and may rotate instead. The X-ray diaphragm and the compensation filter may be controlled according to an angle of the rotation of the C-arm. Thus, a 3-dimensional subtraction process (so-called a rotation DSA) may be applied.

Although the virtual X-ray diaphragm and the virtual compensation filter are set on the replayed fluoroscopic image to set the X-ray diaphragm and the compensation filter in the first embodiment, the X-ray diaphragm and the compensation filter may also be set on the fluoroscopic image displayed in a real time while the X-ray is irradiated to the patient.

As described above, since at least one of the X-ray diaphragm and the compensation filter is controlled according to the position of the X-ray tube, the X-ray diaphragm or the compensation filter can be set at an appropriate position. Therefore, the amount of the X-ray irradiated to the patient is reduced or a halation on the X-ray image may be restrained.

What is claimed is:

1. An X-ray diagnosis apparatus, comprising:
   an X-ray source configured to irradiate an X-ray to an object;

a compensation filter configured to attenuate an amount of the X-ray;

a detector configured to detect the X-ray penetrated through the object;

a movement apparatus configured to move a position of the X-ray source in a first direction parallel to the object; and a controller configured to control the compensation filter to move in a second direction, opposite to the direction of movement of the X-ray source, at a same speed as the movement of the X-ray source.

2. The apparatus of claim 1, further comprising:
a diaphragm configured to restrict an irradiation range of the X-ray; and
a diaphragm controller configured to control the diaphragm based on the position of the X-ray source in the first direction.

3. The X-ray diagnosis apparatus according to claim 2, wherein the movement apparatus is configured to move the position of the X-ray source in a longitudinal direction of the object.

4. The X-ray diagnosis apparatus according to claim 2, wherein the diaphragm controller comprises:
a memory configured to store data of the irradiation range corresponding to the position of the X-ray source; and
a main controller configured to read the data from the memory based on the position of the X-ray.

5. The X-ray diagnosis apparatus according to claim 4, wherein the memory is configured to store the data of the irradiation range corresponding to a plurality of positions of the X-ray source.

6. The X-ray diagnosis apparatus according to claim 2, further comprising an operation unit configured to set the irradiation range on an X-ray fluoroscopic image.

7. The X-ray diagnosis apparatus according to claim 2, wherein the movement apparatus is configured to move the position of the X-ray source along a flow direction of a contrast agent injected into the object, at a desired speed.

8. The X-ray diagnosis apparatus according to claim 2, further comprising a bed on which the object is positioned.

9. The apparatus of claim 1, further comprising:
a diaphragm configured to restrict an irradiation range of the X-ray;
a rotation apparatus configured to rotate a position of the X-ray source around the object; and
a diaphragm controller configured to control the diaphragm based on the position of the X-ray source.

10. The X-ray diagnosis apparatus according to claim 9, wherein the diaphragm controller comprises:
a memory configured to store data of the irradiation range corresponding to the position of the X-ray source; and
a main controller configured to read the data from the memory based on the position of the X-ray.

11. The X-ray diagnosis apparatus according to claim 10, wherein the memory is configured to store the data of the irradiation range corresponding to a plurality of positions of the X-ray source.

12. The X-ray diagnosis apparatus according to claim 9, further comprising an operation unit configured to set the irradiation range on an X-ray fluoroscopic image when the X-ray stops being irradiated.

13. The X-ray diagnosis apparatus according to claim 9, further comprising a bed on which the object is positioned.

14. The apparatus of claim 1, further comprising:
an operation unit configured to set at least one of a virtual diaphragm or a virtual compensation filter on an X-ray fluoroscopic image.

15. The X-ray diagnosis apparatus according to claim 1, wherein the movement apparatus moves the position of the X-ray source in a longitudinal direction of the object.

16. The X-ray diagnosis apparatus according to claim 1, wherein the controller comprises:
a memory configured to store data of an amount of the X-ray corresponding to the position of the X-ray source; and
a main controller configured to read the data from the memory based on the position of the X-ray.

17. The X-ray diagnosis apparatus according to claim 16, wherein the memory is configured to store the data of the amount of the X-ray corresponding to a plurality of the positions of the X-ray source.

18. The X-ray diagnosis apparatus according to claim 1, further comprising an operation unit configured to set the amount of the X-ray on an X-ray fluoroscopic image.

19. The X-ray diagnosis apparatus according to claim 1, wherein the movement apparatus is configured to move the position of the X-ray source along a flow direction of a contrast agent injected into the object at a desired speed.

20. The X-ray diagnosis apparatus according to claim 1, further comprising a bed on which the object is positioned.

21. The apparatus of claim 1, further comprising:
a rotation apparatus configured to rotate a position of the X-ray source around the object; and
the controller is further configured to control the compensation filter based on the position of the X-ray.

22. The X-ray diagnosis apparatus according to claim 21, wherein the controller comprises:
a memory configured to store data of an amount of the X-ray corresponding to the position of the X-ray source; and
a main controller configured to read the data from the memory based on the position of the X-ray.

23. The X-ray diagnosis apparatus according to claim 22, wherein the memory is configured to store the data of the amount of the X-ray corresponding to a plurality of positions of the X-ray source.

24. The X-ray diagnosis apparatus according to claim 21, further comprising an operation unit configured to set the amount of the X-ray on an X-ray fluoroscopic image.

25. The X-ray diagnosis apparatus according to claim 21, further comprising a bed on which the object is positioned.

26. The apparatus of claim 1, further comprising:
a diaphragm configured to restrict an irradiation range of the X-ray; and
means for controlling the diaphragm based on the position of the X-ray source in the first direction.

27. The apparatus of claim 1, further comprising:
a diaphragm configured to restrict an irradiation range of the X-ray;
a rotation apparatus configured to rotate a position of the X-ray source around the object; and
means for controlling the diaphragm based on the position of the X-ray source.

28. A method for obtaining an X-ray image, comprising:
irradiating an X-ray to an object with an X-ray source;
attenuating an amount of the X-ray with a compensation filter;
detecting the X-ray penetrated through the object;
moving a position of the X-ray source in a first direction parallel to the object; and
controlling the compensation filter to move in a second direction, opposite to the direction of movement of the X-ray source, at a same speed as the movement of the X-ray source.

29. A computer readable medium storing instructions for execution on a computer system, which when executed by the computer system, causes the computer system to perform the method recited in claim 28.

30. An X-ray diagnosis apparatus, comprising:
- an X-ray source configured to irradiate an X-ray to an object;
- a compensation filter configured to attenuate an amount of the X-ray;
- a detector configured to detect the X-ray penetrated through the object;
- a movement apparatus configured to move a position of the X-ray source in a direction along the object; and
- means for controlling the compensation filter to move in a second direction, opposite to the direction of movement of the X-ray source, at a same speed as the movement of the X-ray source.

31. The apparatus of claim 30, further comprising:
- a rotation apparatus configured to rotate a position of the X-ray source around the object.

32. The apparatus of claim 31, further comprising:
- a memory configured to store data of an amount of the X-ray corresponding to the position of the X-ray source; and
- a main controller configured to read the data from the memory based on the position of the X-ray and to control the compensation filter based on the data.

33. The apparatus of claim 30, further comprising:
- a memory configured to store data of an amount of the X-ray corresponding to the position of the X-ray source; and
- a main controller configured to read the data from the memory based on the position of the X-ray and to control the compensation filter based on the data.

* * * * *

UNITED STATES PATENT AND TRADEMARK OFFICE
CERTIFICATE OF CORRECTION

PATENT NO. : 7,336,768 B2 Page 1 of 1
APPLICATION NO. : 11/539544
DATED : February 26, 2008
INVENTOR(S) : Ogawa

It is certified that error appears in the above-identified patent and that said Letters Patent is hereby corrected as shown below:

On the title page, Item (73), the Assignee Information is incorrect. Item (73) should read:

-- (73)  Assignee:  Kabushiki Kaisha Toshiba, Tokyo (JP) --

Signed and Sealed this

Tenth Day of June, 2008

JON W. DUDAS
*Director of the United States Patent and Trademark Office*